United States Patent [19]

Cavazza et al.

[11] Patent Number: 4,518,613
[45] Date of Patent: May 21, 1985

[54] THIOALKANOYL-CARNITINES, PROCESS FOR THEIR PREPARATION AND MUCOLYTIC PHARMACEUTICAL COMPOSITIONS CONTAINING SAME

[76] Inventors: Claudio Cavazza, 35, Via Marocco, Rome, Italy, 00144; Maria O. Tinti, 81, Via Ernesto Basile, Rome, Italy, 00180

[21] Appl. No.: 436,190

[22] Filed: Oct. 22, 1982

[30] Foreign Application Priority Data

Dec. 3, 1981 [IT] Italy ............................. 49835 A/81

[51] Int. Cl.$^3$ ................. A61K 31/265; C07C 153/017
[52] U.S. Cl. .................................. 514/513; 260/455 R
[58] Field of Search ...................... 260/455 R; 424/301

[56] References Cited

U.S. PATENT DOCUMENTS 4,327,111 4/1982 Sundeen et al. ............... 260/455 R

Primary Examiner—Henry R. Jiles
Assistant Examiner—Robert C. Whittenbaugh
Attorney, Agent, or Firm—Ladas & Parry

[57] ABSTRACT

Thioalkanoyl-carnitines of general formula (I)

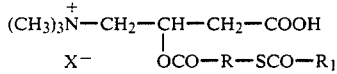

wherein
R is a straight alkylene radical having from 2 to 6 carbon atoms, or is a branched alkylene radical having from 3-6 carbon atoms, or is a branched alkylene radical having from 3-6 carbon atoms, $R_1$ is a straight or branched lower alkyl radical having from 1 to 4 carbon atoms, and $X^-$ is a halogen anion are prepared by reacting a thio-acid (II) of general formula $R_1COSH$ (a) if in (I) the thioalkanoyl radical $R_1COS-$ is in terminal position, with a compound of general formula (III)

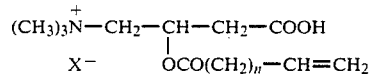

wherein
n is an integer comprised between 0 and 4 or (b) if in (I) the thioalkanoyl radical $R_1COS-$ is not in terminal position, with a compound of general formula (IV)

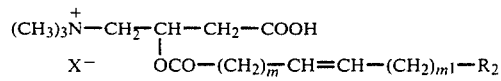

wherein
m and $m^1$ are integers comprised between 0 and 3, and $R_2$ is a lower alkyl radical having from 1 to 4 carbon atoms.

The pharmaceutical compositions containing the thioalkanoyl-carnitines (I) possess mucolytic and antitussive activity.

6 Claims, No Drawings

THIOALKANOYL-CARNITINES, PROCESS FOR THEIR PREPARATION AND MUCOLYTIC PHARMACEUTICAL COMPOSITIONS CONTAINING SAME

The present invention relates to a novel class of thioalkanoyl-carnitines of general formula (I)

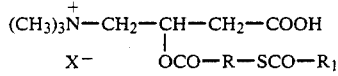

wherein
R is a straight alkylene radical having from 2 to 6 carbon atoms, or is a branched alkylene radical having from 3 to 6 carbon atoms,
$R_1$ is a straight or branched lower alkyl radical having from 1 to 4 carbon atoms, and
$X^-$ is a halogen anion.

It is apparent that, depending on whether R is a straight or branched radical, the thioalkanoyl radical $R_1COS-$ is located in compounds (I) either at terminal or non terminal position.

The compounds of general formula (I) are endowed with remarkable mucolytic and antitussive activity and low toxicity, as will be shown hereinbelow. Therefore, the present invention also relates to pharmaceutical compositions possessing mucolytic and antitussive activity, which comprise as active ingredient at least one of the compounds (I) compounded with the excipients usually employed in the pharmaceutical technology.

Lastly, the invention relates to a process for preparing thioalkanoyl-carnitines (I). This process is characterized in its most general form by:
reacting a thioacid of general formula (II)

wherein $R_1$ has the previously specified meaning,
(a) if in the compounds(I) the thioalkanoyl radical $R_1COS-$ is in terminal position, with a compound of general formula (III)

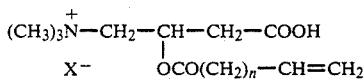

wherein n is an integer comprised between 0 and 4, according to the following reaction scheme:

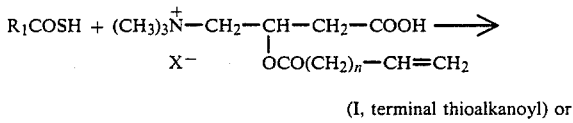

(I, terminal thioalkanoyl) or (b) if in the compounds (I) the thioalkanoyl radical $R_1COS-$ is in non terminal position, with a compound of general formula (IV)

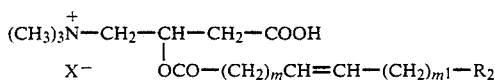

wherein m and $m^1$ are integers comprised between 0 and 3, and
$R_2$ is a lower alkyl radical having from 1 to 4 carbon atoms, according to the following reaction scheme:

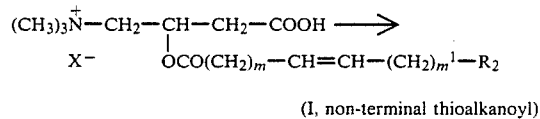

(I, non-terminal thioalkanoyl)

The R radical is preferably selected from the class consisting of ethylene, trimethylene, tetramethylene, ethyl-ethylene, propylene, 1-methyl trimethylene and 2-methyl trimethylene.

The $R_1$ and $R_2$ radicals are preferably selected from the class consisting of methyl, ethyl, propyl, isopropyl and butyl.

The reaction between (II) and (III) and between (II) and (IV) takes place very easily. It is sufficient to contact the reactants with each other even in the absence of solvents and suspending agents and keep the reaction mixture under stirring from a few hours to a few days, at a temperature comprised between about room temperature and 50° C. It is preferable to use an excess of thioacid (II) with respect to (III) and (IV). The excess varies from about 3:1 (molar) if the reaction is carried out in the presence of solvents to 30:1 (molar) in the absence of solvents.

The solvents and suspending agents, if any, and the isolation and purification procedures are those generally used in the organic syntheses.

The following non-limiting examples illustrate the process for preparing some of the compounds of the invention and their chemico-physical characteristics.

EXAMPLE 1

3-thioacetyl propionyl-carnitine (ST 405)

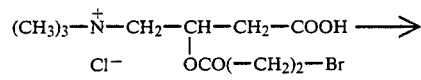

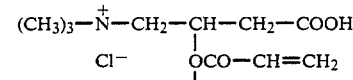

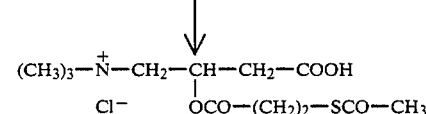

(1) Preparation of acryloyl carnitine

To a solution of 4 grams of bromopropionyl carnitine in 40 ml of $H_2O$ 100 cc of IR 45 amberlite resin activated in OH form were added. The reaction mixture was kept under stirring for 2 hours, then filtered and lyophilized.

The raw material thus obtained was purified by chromatography with silica gel buffered with 1.5% $Na_2HPO_4$ and eluting with methanol. The eluate was treated with HCl and subsequently lyophilized; 1.5 grams of pure product were obtained. Yield 42%

NMR $D_2O\delta6.6–6.3$ (3H, m, $CH=CH_2$); 5.6 (1H, m,

3.8 (2H, m, N+—CH$_2$); 3.3 (9H, s,

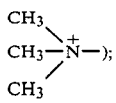

2.6 (2H, d, —CH$_2$CO).

(2) Preparation of 3-thioacetyl propionyl-carnitine

Acryloyl carnitine inner salt (0.008 moles) obtained in the previous step (1) was suspended in 40 ml of absolute ethanol. To the resulting suspension thioacetic acid (0.0238 moles) was added. The suspension was kept under stirring for 3 hours, then precipitated with anhydrous ethyl ether and stored in a refrigerator overnight. An oil precipitated which was separated by decantation and repeatedly purified by dissolving it in ethanol and precipitating it with ethyl ether. The raw material thus obtained was taken up with water, acidified with concentrated HCl at 0° C. and subsequently lyophilized. 1.9 grams of product were obtained. Yield 75%.

NMR D$_2$O δ 5.6 (1H, m,

3.8 (2H, m, N+—CH$_2$—); 3.3 (9H, s, (CH$_3$)$_3$—N+); 3.0–2.6 (6H, m, —C<u>H</u>$_2$COOH, —COC<u>H</u>$_2$C<u>H</u>$_2$—S—); 2.3 (3H, s, —COC<u>H</u>$_3$).

EXAMPLE 2

5-thioacetyl pentanoyl-carnitine (ST 412)

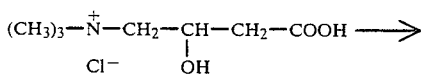

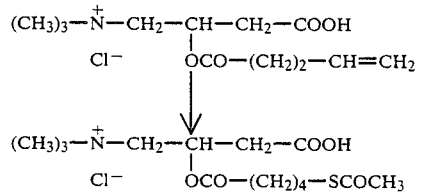

(1) Preparation of allyl acetyl-carnitine.

To a solution of carnitine hydrochloride (9 grams; 0.045 moles) in 15 cc of trifluoroacetic acid, 0.13 moles of allyl acetyl chloride were added. The resulting solution was kept at 45° C. for 4 hours. Subsequently, acetone was added to the solution, the unreacted carnitine was separated and ethyl ether was added, thus obtaining a precipitate. The raw material thus obtained was purified by precipitation from isopropanol—ethyl ether. 9.5 grams of product were obtained. Yield 66%.

NMR D$_2$O δ 5.7 (2H, m, —C<u>H</u>=CH$_2$,

5.1 (2H, m, —CH=C<u>H</u>$_2$—); 3.8 (2H, m, N+—CH$_2$—); 3.3 (9H, s, (CH$_3$)$_3$—N+); 2.8 (2H, d, —C<u>H</u>$_2$COOH; 2.5 (4H, m, —COCH$_2$—CH$_2$—).

(2) Preparation of 5-thioacetyl pentanoyl-carnitine.

22.4 grams (0.38 moles) of thioacetic acid were added to the allyl acetyl carnitine (4 grams; 0.013 moles) of the previous step (1). The resulting solution was kept at 40° C. overnight. Subsequently, ethyl ether was added to the solution and the precipitate thus formed was isolated by decantation. The precipitate was dissolved in water and extracted three times with ethyl ether. The aqueous phase was concentrated and washed with acetone, giving 3.9 grams of product. Yield 84%.

NMR D$_2$O δ 5.6 (1H, m,

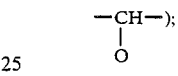

3.7 (2H, m, N+—CH$_2$—); 3.2 (9H, s, (CH$_3$)$_3$—N+—); 2.7 (6H, m, —C<u>H</u>$_2$COOH; OCOC<u>H</u>$_2$—; C<u>H</u>$_2$S); 2.4 (3H, s, —COC<u>H</u>$_3$); 1.6 (4H, m, —COCH$_2$C<u>H</u>$_2$C<u>H</u>$_2$CH$_2$ S—).

EXAMPLE 3

3-thioacetyl butyryl carnitine (ST 406)

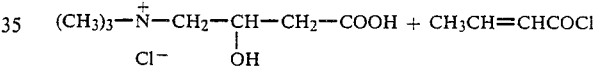

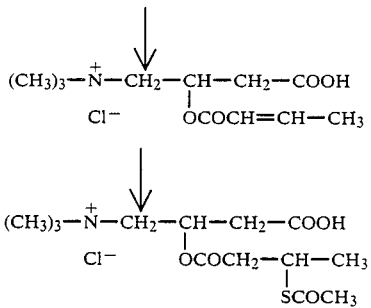

(1) Preparation of crotonoyl carnitine.

8 cc (0.08 moles) of crotonyl chloride were added to a solution of carnitine hydrochloride (8 grams; 0.04 moles) in trifluoroacetic acid. The reaction mixture was kept under stirring at 50° C. overnight. Subsequently, ethyl ether was added to the mixture and a precipitate formed. The precipitate was filtered off and used as such in the subsequent reaction.

NMR D$_2$O δ 7.5–6.9 (1H, m, —OCOC<u>H</u>=CH—); 6.3–5.5 (2H, m, —OCOCH=C<u>H</u>—;

3.8 (2H, m, N+—CH$_2$—); 3.3 (9H, s, (CH$_3$)$_3$—N+); 2.8 (2H, d, —C<u>H</u>$_2$COOH); 2.0 (3H, d, =CH—C<u>H</u>$_3$).

(2) Preparation of 3-thioacetyl butyryl-carnitine.

15 cc (0.20 moles) of thioacetic acid were added to the crotonyl carnitine (3.5 grams; 0.01 moles) of the previous step (1). The reaction mixture was kept under stirring at room temperature for 4 days. Ethyl ether was then added to the reaction mixture. An oil was obtained which was purified by dissolving it in ethanol and precipitating it again with ethyl ether. The precipitation was repeated three times. Subsequently, the precipitate was dissolved in water and extracted three times with ethyl ether. The aqueous solution was lyophilized. 2.6 grams of product were obtained. Yield 70%.

NMR D$_2$O δ 5.5 (1H, m,

); 3.8 (2H, m, N$^+$—CH$_2$—); 3.2 (9H, s, (CH$_3$)$_3$—N$^+$); 2.6–2.9 (4H, m, —CH$_2$COOH; —OCOCH$_2$—); 2.4 (3H, s, —COCH$_3$); 2.2 (1H, m, —CH—SCO—); 1.4 (3H, d, —CH—CH$_3$).

The acute toxicity, the expectorant and mucolytic activities and the effect on ciliar motility of the compounds of formula (I) were studied.

ACUTE TOXICITY

LD50 of the compounds of general formula (I) assessed with the Weil method ("Tables for convenient calculation of median effective dose (LD50 or ED50) and instructions in their use", Biometrics, 249–253, 1952), by e.p. administration in mouse is shown in Table 1.

TABLE 1

LD50 and fiducial limits, mg/Kg e.p., of the compounds of formula (I). Weil method N = 4, K = 4.

| Compound | LD50 | fiducial limits |
|---|---|---|
| ST-405 | 378 | 489–292 |
| ST-406 | 97 | 115–82 |
| ST-412 | 1540 | 1760–1320 |

EXPECTORANT ACTIVITY

The tests were carried out on male rabbits, weighing 2–3 Kg, anesthetized with ethyl urethane, by following the method disclosed by Perry et al. (J. Pharm. Exp. Ther. 73, 65, 1941).

The anesthetized animals, strapped head downward to an operating table at an inclination of 60°, had a cannula inserted in their trachea. Each cannula was connected to a feeding device which delivered a steady flow-rate of pre-heated air (36°–38° C.) at constant humidity (80%). At the lower end of each cannula, a graduated cylinder was fitted, wherein the bronchial secretion was collected. All of the animals breathed spontaneously and consequently they self-regulated the air intake suitable for normal respiration. After an hour following cannula insertion, the animals were administered oraly (by stomach tube) the compounds of general formula (I) dissolved in distilled water at doses comprised between 20 and 40 mg. Each dose of drug was administered to 5 animals. The control animals (8) were given water only. The amount of secretion was determined after 1, 2 and 4 hours from administration. The results, summarized in Table 2, show that the compounds of general formula (I) do not exert expectorant activity.

MUCOLYTIC ACTIVITY

The tests were carried out in vitro by using the method disclosed by Morandini et al. (Lotta contro la tubercolosi 47, n. 4, 1977). A thromboelastograph was used to follow the variations induced by the compounds of general formula (I) and acetylcysteine on the rheological properties of human sputum. The results thereof, summarized in Table 3, show that the compounds of formula (I) bring about a greater decrease of human sputum density than that induced by acetylcysteine.

EFFECT ON CILIAR ACTIVITY

The ability of the compounds of formula (I) to affect the ciliary motility was studied by observing with the microscope the ciliary movement of rat trachea rings soaked in solutions of the test compounds.

By this technique it is possible to study, with relation to compound concentration and contact time, the ciliary movement block provoked by the tests compounds, which is related to mucus clearance from ciliary epithelium.

Substances to be used in the form of solutions must allow the foregoing block not to take place in less than fifteen minutes from contact.

2% aqueous solutions of the compounds of formula (I) provoked the ciliary movement block to take place in 18–22 minutes.

TABLE 2

Effect of compounds of general formula (I) on bronchial secretion

| | Percentage variations ± s.e. of bronchial secretion versus basal values at the following time intervals after administration | | |
|---|---|---|---|
| Compounds | 1 hour | 2 hours | 4 hours |
| Control (H$_2$O) | +1.3 ± 0.04 | +2.2 ± 0.05 | +3.5 ± 0.04 |
| ST-405 | +1.1 ± 0.03 | +1.9 ± 0.04 | +3.6 ± 0.05 |
| ST-406 | +1.4 ± 0.05 | +1.9 ± 0.05 | +3.4 ± 0.04 |
| ST-412 | +1.3 ± 0.04 | +2.1 ± 0.05 | +3.1 ± 0.03 | n = 6 animals per group

TABLE 3

Mucolytic activity in vitro of compounds of general formula (I) and acetylcysteine: modifications of human sputum density;

| | Percentage drop ± s.e. of the tracing versus maximum peak* after addition of 1 ml of a 10% solution of the test compounds at the dilution indicated | |
|---|---|---|
| Compounds | 1/30 | 1/60 |
| ST-405 | 79 | 65 |
| ST-406 | 88 | 70 |
| ST-412 | 87 | 64 |
| Acetylcysteine | 84 | 55 |

*Mucolytic activity index.

As experimentally shown, the compounds of this invention significantly modify the rheological properties of sputum. On perusal of the obtained results a decrease in sputum density at the larger doses (or lower dilutions) and at the smaller doses (or higher dilutions) constantly higher than that provoked by acetylcysteine, is detected. On the other hand none of the compounds increases bronchial secretion nor is able to block the ciliary movement of the epithelium of trachea ring preparations in time intervals shorter than those permitted.

The compounds of the present invention are therapeutically useful for the treatment of the diseases of the respiratory tract. The patients in need thereof will be orally or parenterally administered a therapeutically effective amount of a compound of general formula (I).

The dose of compound of general formula (I) orally or parenterally administered will be generally comprised between about 15 and about 70 mg/Kg of body weight/day, although larger or smaller doses can be administered by the attending physician having regard to the age, weight and general conditions of the patient, utilizing sound professional judgement.

In practice, the compounds are orally or parenterally administered in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials. Hereinbelow some non-limiting examples of compositions suitable for oral or parenteral administration are given.

PHARMACEUTICAL COMPOSITIONS

| | |
|---|---|
| Ampoules for aerosol administration or intramuscular administration | |
| Each ampoule contains: | |
| ST-405 | 0.40 g |
| sodium metabisulfite | 10 mg |
| pyrogen-fre, distilled water | 3 ml |
| Syrup | |
| ST-405 | 4.0 g |
| sorbitol, 70 percent | 15 g |
| sucrose | 50 g |
| ethanol | 1 ml |
| p-hydroxybenzoate | 0.2 mg |
| flavoring agents | 0.5 ml |
| distilled water | q.s. to 100 ml |
| saccharin | 0.20 g |
| Suppositories for Adults | |
| ST-405 | 0.40 g |
| sodium metabisulfite | 0.020 g |
| excipients q.s. to 1 suppository | |
| Pediatric Suppositories | |
| ST-405 | 0.20 g |
| sodium metabisulfite | 0.010 g |
| excipient q.s. to 1 suppository | |
| Suppositories for unweaned babies | |
| ST-405 | 0.10 g |
| sodium metabisulfite | 0.005 g |
| excipient q.s. to 1 suppository | |
| Single-dose sachets (5 g) | |
| Each 100 grams contain: | |
| ST-405 | 3.80 g |
| saccharin | 0.20 g |
| orange flavour | 0.5 g |
| orange lyophilyzate | 10 g |
| sucrose, balance to 100 grams | |

What is claimed is:

1. A compound of the formula $$(CH_3)_3\overset{+}{N}-CH_2-CH-CH_2-COOH$$
$$X^- \quad\quad OCO-R-SCO-R_1$$

wherein

R is a straight alkylene radical having from 2 to 6 carbon atoms, or is a branched alkylene radical having from 3 to 6 carbon atoms, $R_1$ is a straight or branched lower alkyl radical having from 1 to 4 carbon atoms, and $X^-$ is a halogen anion.

2. The compound of claim 1, 3-thioacetyl propionylcarnitine.

3. The compound of claim 1, 5-thioacetyl pentanoylcarnitine.

4. The compound of claim 1, 3-thioacetyl-butyrylcarnitine.

5. A pharmaceutical composition possessing mucolytic and antitussive activities, comprising a therapeutically effective amount of at least one of a compound according to claim 1 as active component plus an inert diluent.

6. A process for preparing a compound according to claim 1, which comprises
reacting a thioacid of the formula $$R_1COSH$$

wherein $R_1$ has the previously specified meaning with a compound of the formula $$(CH_3)_3\overset{+}{N}-CH_2-CH-CH_2-COOH \quad\quad (a)$$
$$X^- \quad\quad OCO(CH_2)_n-CH=CH_2$$

wherein n is an integer comprised between 0 and 4, or $$(CH_3)_3\overset{+}{N}-CH_2-CH-CH_2-COOH \quad\quad (b)$$
$$X^- \quad\quad OCO(CH_2)_mCH=CH-(CH_2)_{m^1}-R_2$$

wherein m and $m^1$ are integers comprised between 0 and 3, and $R^2$ is a lower alkyl radical having from 1 to 4 carbon atoms.

* * * * *

UNITED STATES PATENT AND TRADEMARK OFFICE
CERTIFICATE OF CORRECTION

PATENT NO. : 4,518,613
DATED : MAY 21, 1985
INVENTOR(S) : Claudio CAVAZZA ET AL

It is certified that error appears in the above-identified patent and that said Letters Patent is hereby corrected as shown below:

[57] Title page, in the abstract, second column, lines 1-2 delete "or is a branched alkylene radical having from 3-6 carbon atoms"

Signed and Sealed this

Twenty-sixth Day of August 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,518,613
DATED : May 21, 1985
INVENTOR(S) : Claudio Cavazza

It is certified that error appears in the above-identified patent and that said Letters Patent is hereby corrected as shown below:

[73] Title, Page, first column, insert --Assignee:

Sigma-Tau Industrie Farmaceutiche Riunite, S.p.A.

Rome, Italy

Signed and Sealed this

Tenth Day of January, 1989

Attest:

DONALD J. QUIGG

*Attesting Officer*        *Commissioner of Patents and Trademarks*